United States Patent [19]

Pretzer et al.

[11] 4,151,208

[45] Apr. 24, 1979

[54] PROCESS FOR THE SELECTIVE PREPARATION OF ACETALDEHYDE FROM METHANOL AND SYNTHESIS GAS

[75] Inventors: Wayne R. Pretzer, Oakmont Borough; Thaddeus P. Kobylinski, Gibsonia; John E. Bozik, Plum Borough, all of Pa.

[73] Assignee: Gulf Research & Development Company, Pittsburgh, Pa.

[21] Appl. No.: 863,744

[22] Filed: Dec. 23, 1977

[51] Int. Cl.² ............................................. C07C 47/06
[52] U.S. Cl. ................................................. 260/601 R
[58] Field of Search ........................ 260/601 R, 604 R

[56] References Cited

U.S. PATENT DOCUMENTS

| 3,356,734 | 12/1967 | Kurahhi et al. | 260/601 R |
| 3,996,288 | 12/1976 | Yukatu | 260/599 |

*Primary Examiner*—Werren B. Lone
*Attorney, Agent, or Firm*—Cleveland R. Williams

[57] ABSTRACT

A process for selectively producing acetaldehyde which comprises contacting methanol, hydrogen and carbon monoxide with cobalt (II) meso-tetraaromaticporphine and an iodine promoter.

12 Claims, No Drawings

PROCESS FOR THE SELECTIVE PREPARATION OF ACETALDEHYDE FROM METHANOL AND SYNTHESIS GAS

BACKGROUND OF THE INVENTION

1. Field of the Invention

The synthesis of aliphatic hydrocarbons, such as aldehydes, alcohols, etc., by reacting methanol with synthesis gas (hydrogen and carbon monoxide) is not a new concept. Processes are available for producing a wide spectrum of hydrocarbons, such as alcohols, aldehydes, ketones, esters, ethers and fatty acids of almost any chain length and degree of saturation. The relative amount or extent to which one or more of the above-described products is obtained is determined and/or controlled by the type catalyst used in the reaction. Catalysts which have been used in the past to produce aldehydes, alcohols, etc., are those selected from iron, cobalt, nickel, zinc and the like on a support, either alone or in combination with one or more promoter(s).

The conversion of an alcohol, for example, methanol, to an aldehyde, such as acetaldehyde, containing one carbon atom more than the original alcohol is normally a tedious and time-consuming procedure involving a series of steps. Additionally, catalysts which possess acceptable activity generally tend to give a wide spectrum of products, for example, hydrocarbons and oxygenated hydrocarbons having a broad distribution of carbon atoms. This not only complicates the separation and recovery of desired products, but results in reduced yield of said desired products and erosion of reactants in the production of undesirable products. The process herein is particularly suited to the selective formation of acetaldehyde from methanol and synthesis gas using a cobalt (II) meso-tetraaromaticporphine in combination with an iodine promoter.

2. Description of the Prior Art

The reaction of methanol with hydrogen and carbon monoxide to produce acetaldehyde is appreciated and disclosed by the prior art. However, most known processes produce an undesirably large mixture of alcohols, ketones and carboxylic acids in addition to the desired aldehyde.

U.S. Pat. No. 3,356,734, issued to Kurahhi et al., on Dec. 5, 1967, entitled "Process for the Production of Acetaldehyde", teaches a process for the production of acetaldehyde in two steps. In the first step, methanol, hydrogen and carbon monoxide are contacted with a cobalt catalyst and a halogen promoter to form a product predominating in acetals. The cobalt catalyst described is selected from cobalt salts which are soluble in methanol. In particular, preferred soluble salts include cobalt acetate, cobalt bromide, chlorate, chloride, iodide, sulfide and the like. The halogen promoter is selected from iodine, bromine, chlorine and the like. In the second step, the acetals so produced are contacted with a second distinct catalyst system to hydrolyze the acetals to acetaldehyde and methanol. Maximum possible selectivity to acetaldehyde is from about 17 to about 38 mol percent of the converted methanol.

SUMMARY OF THE INVENTION

The present invention relates to a process for the selective production of acetaldehyde from methanol wherein methanol is reacted with hydrogen and carbon monoxide in the presence of a catalyst under reaction conditions, the improvement which comprises contacting methanol, hydrogen and carbon monoxide with a cobalt (II) meso-tetraaromaticporphine and an iodine promoter under reaction temperature and pressure for a time period sufficient to convert methanol to acetaldehyde.

DESCRIPTION OF THE INVENTION

The present invention relates to a process for the selective formation of acetaldehyde from methanol which comprises contacting methanol, hydrogen and carbon monoxide with a cobalt (II) meso-tetraaromaticporphine, a method of preparation for said compounds is located in the Journal of American Chemical Society, P. Rothemund and A. R. Menotti, V. 70, page 1808 (1948), and an iodine promoter under reaction conditions for a time period sufficient to produce said acetaldehyde. Although hydrogen and carbon monoxide are employed herein for reaction with methanol to produce acetaldehyde, it is understood that any combination of compounds that will form hydrogen and carbon monoxide in the reaction zone can also be used, for example, mixtures of hydrogen and carbon dioxide or water and carbon monoxide, etc.

The mixture of hydrogen and carbon monoxide, used herein, can be produced from anything containing carbon and hydrogen. Two types of reactions, for example, can be used for the production of synthesis gas, for example, partial oxidation and steam reforming. Steam reforming is the more important process when natural gas (methane) is the hydrogen-carbon source. Partial oxidation is used primarily for heavy fuel and residue. The relative amounts of hydrogen and carbon monoxide present in the reaction mixture can be varied over a wide range. However, in general, the molar ratio range of hydrogen to carbon monoxide is from about 10:1 to about 1:10, especially from about 3:1 to about 1:3, however, conventional synthesis gas (mixtures of hydrogen and carbon monoxide) with a molar ratio of about 1:1 is convenient and satisfactory for the process herein. It is to be noted that molar ratios outside the aforestated ratio ranges can be employed herein and, as pointed out hereinabove, compounds or reaction mixtures which give rise to the formation of carbon monoxide and hydrogen can be used instead of mixtures comprising hydrogen and carbon monoxide which are used in the preferred embodiments of this invention.

In a preferred embodiment, methanol, hydrogen and carbon monoxide are introduced into a pressure-resistant reaction vessel, for example, a stainless steel autoclave with agitation means. Agitation is defined herein as shaking, rocking, stirring, percolation with synthesis gas, etc. Methanol can be converted into acetaldehyde in a batch operation or in a continuous process. When the batch method is used, methanol, hydrogen, carbon monoxide, a cobalt (II) meso-tetraaromaticporphine, and iodine promoter are introduced into the reaction vessel and the pressure and temperature are adjusted to the operating reaction conditions. If the system is a closed system, the pressure is raised to the desired level with hydrogen and carbon monoxide before the reaction is initiated and the pressure falls as the reaction proceeds, but never below reaction pressure. Alternatively, the system can be equipped with a reservoir which contains synthesis gas and which feeds said gas to the reaction vessel at a set pressure on demand, thus maintaining a particular pressure level.

In a continuous process for producing acetaldehyde, methanol, hydrogen, carbon monoxide, cobalt (II)

meso-tetraaromaticporphine and iodine promoter are, for example, continuously fed into a pressure-resistant reaction vessel substantially as described herein at a constant rate or even a variable rate. The cobalt (II) meso-tetraaromaticporphine and iodine promoter are normally dissolved in an inert solvent, for example, ethylene glycol, 1,2-dimethoxy ethane, or octane, before introduction into the reaction vessel for ease of application and recovery of the cobalt (II) meso-tetraaromaticporphine and iodine promoter. The mixture of methanol, hydrogen, carbon monoxide cobalt (II) meso-tetraaromaticporphine, and iodine promoter is next reacted under reaction conditions for a time period sufficient to convert methanol to acetaldehyde. Generally, the methanol and cobalt (II) meso-tetraaromaticporphine are mixed together in a molar ratio range of from about 1:1 to about 100,000:1, preferably from about 1:1 to about 2,000:1.

Pressures which are suitable for use in our process, for example, generally are above about 1000 psig (6.83 MPA), but should not be in excess of about 10,000 psig (68.30 MPA). An especially desirable pressure range is from about 1000 psig (6.83 MPA) to about 6000 psig (40.98 MPA), preferably from about 2000 psig (13.66 MPA) to about 5000 psig (34.15 MPA). Temperatures which are suitable for use in our process, for example, are those temperatures which initiate a reaction between the reactants herein to produce acetaldehyde, generally from about 150° C. to about 250° C., preferably from about 175° C. to about 225° C. The reaction is conducted for a time period sufficient to convert methanol to acetaldehyde, normally from about 0.5 hour to about 10 hours, especially from about 1 hour to about 5 hours. Recovery of the desired acetaldehyde from the reaction product can be effected in any convenient or conventional manner, for example, by distillation or the like, for example, at ambient pressure and 21° C., the components will distill off in the following sequence for the desired recovery: dimethyl ether, acetaldehyde, methylacetate, methanol and ethanol.

The cobalt (II) meso-tetraaromaticporphine and iodine promoter herein are highly selective to the formation of acetaldehyde and minimize the formation of undesirable by-products such as ethanol, ethers, esters and other alcohol derivatives. It should be noted that the cobalt (II) meso-tetraaromaticporphine in combination with the iodine promoter herein is selective to the formation of at least 60 percent acetaldehyde from the converted methanol.

While almost any soluble source of cobalt can be used to produce a mixture containing some acetaldehyde from methanol, carbon monoxide and hydrogen, most cobalt sources, however, have the disadvantage of producing a wide variety of alcohols and their derivatives from the above reactants and do not optimize the formation of acetaldehyde. We have discovered when the cobalt source is a meso-tetraaromaticphorphine, excellent selectivity to acetaldehyde results. Specific examples of cobalt (II) meso-tetraaromaticporphines that can be used herein include cobalt (II) meso-tetraphenylporphine, cobalt (II) meso-tetra(4-pyridyl)porphine, cobalt (II) meso-tetra(4-carboxyphenyl)porphine, cobalt (II) meso-tetra(4-N-methylpyridyl)porphine iodide, and sodium cobalt (II) meso-tetra(4-sulfonatophenyl)porphine.

Any source of iodine which is capable of dissassociating in the reaction medium (i.e., ionizing to form free iodine ions) can be used as a promoter in the present invention. Illustrative examples of iodine promoters especially suitable for use herein include iodine, potassium iodide, calcium iodide, sodium iodide, lithium iodide, hydrogen iodide, methyl iodide, ethyl iodide and the like. Generally, the cobalt (II) meso-tetraaromaticporphine and iodine promoter, herein, are mixed in a molar ratio range of from about 100:1 to about 1:100, preferably from about 10:1 to about 1:10.

DESCRIPTION OF PREFERRED EMBODIMENT

The following serves to further illustrate and instruct one skilled in the art the best mode of how to practice this invention and is not intended to be construed as limiting thereof.

Into a 330 cc stainless steel pressure-resistant autoclave were charged 3 millimoles of cobalt (II) meso-tetraphenylporphine, 0.75 millimole of iodine and 100 milliliters of methanol. The reactor was next purged twice with nitrogen gas and then pressurized with synthesis gas (hydrogen to carbon monoxide molar ratio=1:1) to a pressure of about 1000 psig (6.83 MPA) lower than the desired working pressure. The system was then heated to a temperature of about 200° C. and the pressure was adjusted to about 4000 psig (27.6 MPA). The reaction was allowed to proceed for approximately three hours, after which the reactor was cooled by an internal cooling coil to about −75° C. The reactor was vented through a dry gas meter, a gas sample was taken for mass spectral analysis, and the liquid product was analyzed using a model 900 Perkin-Elmer gas chromatograph utilizing a 16 ft (4.88 meters)×⅛ in (0.32 centimeter) stainless steel column wherein 8 ft (2.44 meters) of the column were packed with 80/100 mesh Poropak Q and the other 8 ft (2.44 meters) were packed with 80/100 mesh Poropak R. It is to be noted that Poropak Q and Poropak R are a form of polyvinyl benzene marketed commercially by Waters Associates, a corporation located in Milford, Massachusetts. The gas chromatograph was programmed to increase from 40° C. to 190° C. at a rate of 32° C./min and with a helium flow rate at 30 cc/minute.

The analysis indicated that 67.9% of the methanol was converted with the following mole percent selectivity:

| Compound | Selectivity, Mole % |
|---|---|
| Acetaldehyde | 62.3 |
| Dimethyl Ether | 9.3 |
| Ethanol | 11.4 |
| Methyl Acetate | 12.9 |
| Unknown | 4.1 |

From the data above, it is readily apparent that the cobalt (II) meso-tetraphenylporphine in combination with an iodine gives excellent selectivity in the conversion of methanol to acetaldehyde in a single step. It is to be noted that any of the cobalt (II) meso-tetraaromaticporphine compounds can be substituted for the cobalt (II) meso-tetraphenylporphine above with substantially the same results. It should additionally be noted, that the other iodine promoters herein can be substituted for the iodine used in this example with similar results.

Obviously, many modifications and variations of the invention, as hereinabove set forth, can be made without departing from the spirit and scope thereof, and therefore only such limitations should be imposed as are indicated in the appended claims.

We claim:

1. In a process for the production of acetaldehyde from methanol wherein methanol is reacted with hydrogen and carbon monoxide in the presence of a catalyst, the improvement which comprises contacting methanol, hydrogen and carbon monoxide with cobalt (II) meso-tetraaromaticporphine and an iodine promoter, at a hydrogen and carbon monoxide molar ratio of from about 10:1 to about 1:10, a methanol and cobalt (II) meso-tetraaromaticporphine molar ratio of from about 1:1 to about 100,000:1, a cobalt (II) meso-tetraaromaticporphine and iodine promoter molar ratio of from about 100:1 to about 1:100, a reaction temperature of from about 150° C. to about 250° C., and a reaction pressure of from about 1000 psig. (6.83 MPa) to about 6000 psig. (40.98 MPa), for a reaction time period sufficient to convert methanol to acetaldehyde.

2. The process of claim 1 wherein said cobalt (II) meso-tetraaromaticporphine is a member selected from the group consisting of cobalt (II) meso-tetraphenylporphine, cobalt (II) meso-tetra(4 pyridyl)porphine, cobalt (II) meso-tetra(4-carboxyphenyl)porphine, cobalt (II) meso-tetra(4-N-pyridylphenyl)porphine, and sodium cobalt (II) meso-tetra(4-sulfonatophenyl)porphine.

3. The process of claim 1 wherein said cobalt (II) meso-tetraaromaticporphine is cobalt (II) meso-tetraphenylporphine.

4. The process according to claim 1 wherein the hydrogen and carbon monoxide are in a molar ratio of from about 3:1 to about 1:3.

5. The process of claim 1 wherein the methanol and cobalt (II) meso-tetraaromaticporphine are in a molar ratio of from about 1:1 to about 2,000:1.

6. The process of claim 1 wherein the cobalt (II) meso-tetraaromaticporphine and iodine promoter are in a molar ratio of from about 10:1 to about 1:10.

7. The process of claim 1 wherein the iodine promoter is a member selected from the group consisting of iodine, potassium iodide, calcium iodide, sodium iodide, lithium iodide, hydrogen iodide, methyl iodide and ethyl iodide.

8. The process of claim 1 wherein the iodine promoter is iodine.

9. The process according to claim 1 having a reaction temperature from about 175° C. to about 225° C.

10. The process of claim 1 having a reaction pressure from about 2000 psig (13.66 MPA) to about 5000 psig (34.15 MPA).

11. The process of claim 1 having a reaction time period from about 0.5 hour to about 10 hours.

12. The process of claim 1 having a reaction time period from about 1 hour to about 5 hours.

* * * * *